(12) United States Patent
Brown

(10) Patent No.: US 6,383,457 B1
(45) Date of Patent: May 7, 2002

(54) TOILET PLUNGER SANITIZING AND STORAGE CONTAINER SYSTEM

(76) Inventor: Movia E. Brown, 14846 SW. 168 Ter., Miami, FL (US) 33187

(*) Notice: Subject to any disclaimer, the term of this patent is extended or adjusted under 35 U.S.C. 154(b) by 0 days.

(21) Appl. No.: 09/932,690

(22) Filed: Aug. 16, 2001

(51) Int. Cl.⁷ .................................................. A61L 2/18
(52) U.S. Cl. ........................ 422/300; 422/301; 206/209; 206/349; 134/42
(58) Field of Search ................................ 422/300, 301; 206/349, 209

(56) References Cited

U.S. PATENT DOCUMENTS 5,958,150 A * 9/1999 Borger et al. .................. 134/42
6,213,777 B1 * 4/2001 Seitzinger .................... 433/229

* cited by examiner

Primary Examiner—Robert J. Warden, Sr.
Assistant Examiner—Sean E. Conley
(74) Attorney, Agent, or Firm—Joseph N. Breaux

(57) ABSTRACT

A toilet plunger sanitizing and storage container system that includes an innocuous looking, cylinder-shaped, fluid impermeable, main toilet plunger container sealable with a container sealing lid. The system also including a toilet plunger lifter assembly and a quantity of disinfectant solution carried in the lifter assembly. The lifter assembly being sealable along with a plunger assembly within the innocuous looking, cylinder-shaped, fluid impermeable, main toilet plunger container.

Because the toilet plunger is unsanitary after it is used, it would be a further benefit to have a toilet plunger sanitizing and storage container system that included a toilet plunger lifter having a combination plunger and plunger disinfectant holding cup provided with an elongated lifting handle such that, in use, the combination plunger and plunger disinfectant holding cup could be placed under the recently used plunger while the recently used plunger was still positioned above the toilet bowl and preventing any unsanitary drippings from the plunger from dropping onto the toilet seat or area surrounding the toilet while the plunger is transferred back into its innocuous looking, sealable, plunger holding assembly.

1 Claim, 2 Drawing Sheets

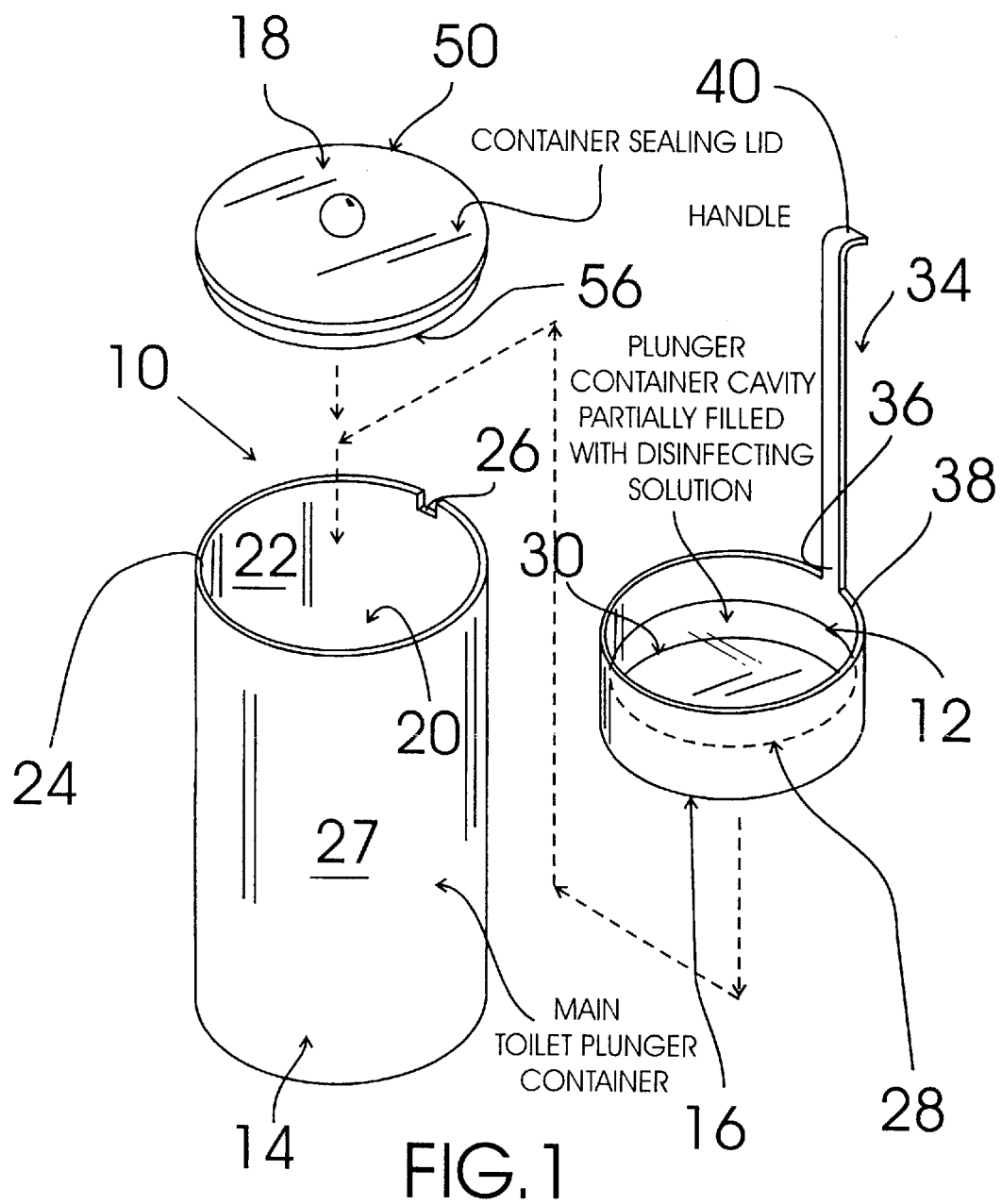

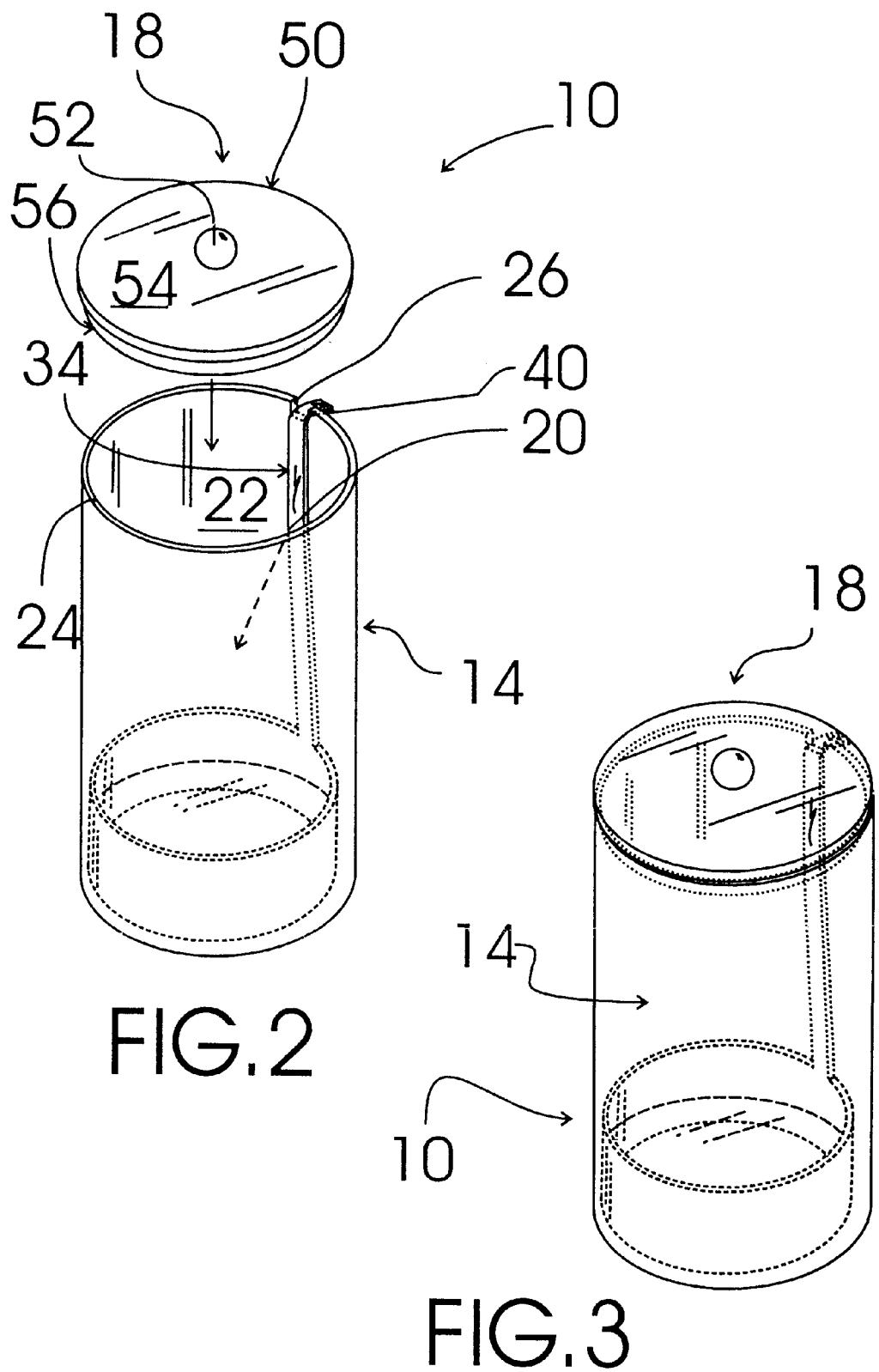

TOILET PLUNGER SANITIZING AND STORAGE CONTAINER SYSTEM

TECHNICAL FIELD

The present invention relates to bathroom accessories and more particularly to a toilet plunger sanitizing and storage container system that includes a quantity of a disinfecting solution, a cylinder-shaped, fluid impermeable, main toilet plunger container having a plunger container cavity formed therein, a container top opening defined by a container top edge, and a lifting handle indentation defined by the container top edge; a toilet plunger lifter assembly including a combination plunger/plunger disinfectant holding cup having an exterior sized to slidably fit into the plunger container cavity and a disinfectant solution holding cavity sized to receive a plunger and constructed from fluid impermeable plastic, the quantity of the disinfecting solution positioned within the disinfectant solution holding cavity, and a lifter assembly handle having a bottom handle end formed with a top edge of the plunger/plunger disinfectant holding cup, a top lifting handle end oriented perpendicular to the bottom handle end and sized to sealing fit into the lifting handle indentation defined by the container top edge; and a container sealing lid including a top cover member having a handle extending from a top surface thereof and a resilient, cylinder-shaped sealing gasket extending from a center of a bottom cover member surface and sized to sealing fit into the container top opening in a manner to seal the plunger container cavity whether the top lifting handle end is or is not positioned in the lifting handle indentation.

BACKGROUND ART

Having a toilet plunger near a toilet to be of use when needed can be a decorating and sanitary problem. It would be desirable, therefore, to have a toilet plunger sanitizing and storage container system that included an innocuous looking, sealable, plunger holding assembly that could be provided with disinfecting liquids therein so that a disinfected, toilet plunger could be positioned adjacent the toilet, hidden within a sealed innocuous looking, sealable, plunger holding assembly. Because the toilet plunger is unsanitary after it is used, it would be a further benefit to have a toilet plunger sanitizing and storage container system that included a toilet plunger lifter having a combination plunger and plunger disinfectant holding cup provided with an elongated lifting handle such that, in use, the combination plunger and plunger disinfectant holding cup could be placed under the recently used plunger while the recently used plunger was still positioned above the toilet bowl and preventing any unsanitary drippings from the plunger from dropping onto the toilet seat or area surrounding the toilet while the plunger is transferred back into its innocuous looking, sealable, plunger holding assembly.

GENERAL SUMMARY DISCUSSION OF INVENTION

It is thus an object of the invention to provide a toilet plunger sanitizing and storage container system that includes a quantity of a disinfecting solution, a cylinder-shaped, fluid impermeable, main toilet plunger container having a plunger container cavity formed therein, a container top opening defined by a container top edge, and a lifting handle indentation defined by the container top edge; a toilet plunger lifter assembly including a combination plunger/plunger disinfectant holding cup having an exterior sized to slidably fit into the plunger container cavity and a disinfectant solution holding cavity sized to receive a plunger and constructed from fluid impermeable plastic, the quantity of the disinfecting solution positioned within the disinfectant solution holding cavity, and a lifter assembly handle having a bottom handle end formed with a top edge of the plunger/plunger disinfectant holding cup, a top lifting handle end oriented perpendicular to the bottom handle end and sized to sealing fit into the lifting handle indentation defined by the container top edge; and a container sealing lid including a top cover member having a handle extending from a top surface thereof and a resilient, cylinder-shaped sealing gasket extending from a center of a bottom cover member surface and sized to sealing fit into the container top opening in a manner to seal the plunger container cavity whether the top lifting handle end is or is not positioned in the lifting handle indentation.

Accordingly, a toilet plunger sanitizing and storage container system is provided. The a toilet plunger sanitizing and storage container system includes a quantity of a disinfecting solution, a cylinder-shaped, fluid impermeable, main toilet plunger container having a plunger container cavity formed therein, a container top opening defined by a container top edge, and a lifting handle indentation defined by the container top edge; a toilet plunger lifter assembly including a combination plunger/plunger disinfectant holding cup having an exterior sized to slidably fit into the plunger container cavity and a disinfectant solution holding cavity sized to receive a plunger and constructed from fluid impermeable plastic, the quantity of the disinfecting solution positioned within the disinfectant solution holding cavity, and a lifter assembly handle having a bottom handle end formed with a top edge of the plunger/plunger disinfectant holding cup, a top lifting handle end oriented perpendicular to the bottom handle end and sized to sealing fit into the lifting handle indentation defined by the container top edge; and a container sealing lid including a top cover member having a handle extending from a top surface thereof and a resilient, cylinder-shaped sealing gasket extending from a center of a bottom cover member surface and sized to sealing fit into the container top opening in a manner to seal the plunger container cavity whether the top lifting handle end is or is not positioned in the lifting handle indentation.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 1 is an exploded perspective view of an exemplary embodiment of the toilet plunger sanitizing and storage container system of the present invention showing a quantity of the disinfecting solution; the cylinder-shaped, fluid impermeable, main toilet plunger container; the toilet plunger lifter assembly; and the container sealing lid.

FIG. 2 is a partially exploded perspective view of the exemplary toilet plunger sanitizing and storage container system of FIG. 1 showing the toilet plunger lifter assembly with the combination plunger/plunger disinfectant holding cup positioned within the cylinder-shaped, fluid impermeable, main toilet plunger container; the quantity of the disinfecting solution contained within the combination plunger/plunger disinfectant holding cup; and the container sealing lid positioned above the container top opening.

FIG. 3 is a perspective view of the toilet plunger sanitizing and storage container system of FIG. 1 in the sealed configuration.

EXEMPLARY MODE FOR CARRYING OUT THE INVENTION

FIGS. 1–3 show various aspects of an exemplary embodiment of the toilet plunger sanitizing and storage container system of the present invention generally designated 10. Toilet plunger sanitizing and storage container system 10 includes a quantity of the disinfecting alcohol solution, generally designated 12; a cylinder-shaped, fluid impermeable, main toilet plunger container, generally designated 14; a toilet plunger lifter assembly, generally designated 16; and a container sealing lid, generally designated 18.

Cylinder-shaped, fluid impermeable, main toilet plunger container 14 has a plunger container cavity, generally designated 20 formed therein, a circular, container top opening 22 defined by a container top edge 24, and a lifting handle indentation 26 defined by the container top edge 24. The exterior surface 27 of cylinder-shaped, fluid impermeable, main toilet plunger container 14 may be provided with printed decorations or the exterior surface 27 may be shaped, during molding so as to have a decorative shape or shapes thereon.

Toilet plunger lifter assembly 16 includes a combination plunger/plunger disinfectant holding cup, generally designated 28, having an exterior sized to slidably fit into plunger container cavity 20 through top opening 22 and a disinfectant solution holding cavity, generally designated 30, sized to receive a plunger and constructed from fluid impermeable plastic. The quantity of disinfecting alcohol solution 12 is positioned within disinfectant solution holding cavity 30. Toilet plunger lifter assembly 16 also includes a lifter assembly handle, generally designated 34, having a bottom handle end 36 integrally formed with a top edge 38 of plunger/plunger disinfectant holding cup 28 and a top lifting handle end 40 oriented perpendicular to bottom handle end 36 and sized to sealing fit into lifting handle indentation 26 defined by container top edge 24.

Container sealing lid 18 including a top cover member, generally designated 50, having a ball-shaped, handle 52 extending from a top surface 54 thereof and a resilient, cylinder-shaped sealing gasket, generally designated 56, extending from a center of a bottom cover member surface and sized to sealing fit into the container top opening 22 in a manner to seal the plunger container cavity 20 whether top lifting handle end 40 is or is not positioned in lifting handle indentation 26.

It can be seen from the preceding description that a toilet plunger sanitizing and storage container system has been provided.

It is noted that the embodiment of the toilet plunger sanitizing and storage container system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A toilet plunger sanitizing and storage container system comprising:

a disinfecting solution;

a cylinder-shaped, fluid impermeable, main toilet plunger container having a plunger container cavity formed therein, a container top opening defined by a container top edge, and a lifting handle indentation defined by the container top edge;

a toilet plunger lifter assembly including a combination plunger/plunger disinfectant holding cup having an exterior sized to slidably fit into the plunger container cavity and a disinfectant solution holding cavity sized to receive a plunger and constructed from fluid impermeable plastic, and a lifter assembly handle having a bottom handle end formed with a top edge of the plunger/plunger disinfectant holding cup, a top lifting handle end oriented perpendicular to the bottom handle end and sized to sealing fit into the lifting handle indentation defined by the container top edge, the quantity of the disinfecting solution positioned within the disinfectant solution holding cavity; and a container sealing lid including a top cover member having a handle extending from a top surface thereof and a resilient, cylinder-shaped sealing gasket extending from a center of a bottom cover member surface and sized to sealing fit into the container top opening in a manner to seal the plunger container cavity whether the top lifting handle end is or is not positioned in the lifting handle indentation.

* * * * *